US00PP19986P3

(12) United States Plant Patent
Hambali

(10) Patent No.: US PP19,986 P3
(45) Date of Patent: May 12, 2009

(54) ***AGLAONEMA* PLANT NAMED 'TWYAG0042'**

(50) Latin Name: ***Aglaonema* hybrid**
Varietal Denomination: TWYAG0042

(75) Inventor: Gregori G. Hambali, Bogor (ID)

(73) Assignee: Kerry's Bromeliad Nursery, Inc., Apopka, FL (US)

( * ) Notice: Subject to any disclaimer, the term of this patent is extended or adjusted under 35 U.S.C. 154(b) by 20 days.

(21) Appl. No.: 11/904,507

(22) Filed: Sep. 28, 2007

(65) Prior Publication Data

US 2009/0089903 P1 Apr. 2, 2009

(51) Int. Cl.
*A01H 5/00* (2006.01)

(52) U.S. Cl. ..... Plt./376

(58) Field of Classification Search ..... Plt./376
See application file for complete search history.

*Primary Examiner*—Annette H Para
*Assistant Examiner*—Louanne C Krawczewicz Myers
(74) *Attorney, Agent, or Firm*—Jondle & Associates, P.C.

(57) ABSTRACT

A new *Aglaonema* plant particularly distinguished by being small in stature and having foliage that is medium-green and marked, especially proximally, with small coalescing yellow-green spots and blotches, areas adjacent to the primary veins are often variably marked with yellow-green and occasionally tinged with pink, areas adjacent to the midrib are marked with yellow-green and often variably tinged with pink, primary veins are yellow-green with occasional tinges of pink while the midrib is pink, is disclosed.

1 Drawing Sheet

Genus and species: *Aglaonema* hybrid.
Variety denomination: 'TWYAG0042'.

BACKGROUND OF THE NEW PLANT

The present invention comprises a new and distinct cultivar of *Aglaonema*, botanically known as *Aglaonema* hybrid and hereinafter referred to by the variety name as 'TWYAG0042'. The new variety originated from an open pollination made in Bogor, West Java, Indonesia between unknown individual plants of *Aglaonema* (species unknown). The new variety was discovered as a single plant within the progeny of the stated open pollination in a controlled environment in Bogor, West Java, Indonesia.

The new variety was created in Bogor, West Java, Indonesia and has been asexually reproduced repeatedly by vegetative cuttings and tissue culture in Apopka, Fla. for two or more generations. The present invention has been found to retain its distinctive characteristics through successive asexual propagations.

SUMMARY OF THE INVENTION

The following are the most outstanding and distinguishing characteristics of the new variety when grown under normal horticultural practices in Apopka, Fla.

1. Foliage that is medium-green and marked, especially proximally, with small coalescing yellow-green spots and blotches;
2. Areas adjacent to the primary veins are often variably marked with yellow-green and occasionally tinged with pink;
3. Areas adjacent to the midrib are marked with yellow-green and often variably tinged with pink;
4. Primary veins are yellow-green with occasional tinges of pink while the midrib is pink; and
5. Small in stature.

DESCRIPTION OF THE PHOTOGRAPHS

This new *Aglaonema* plant is illustrated by the accompanying photographs which show the overall plant habit and color and shape of the upper and lower surfaces of the leaves. The colors shown are as true as can be reasonably obtained by conventional photographic procedures.

DESCRIPTION OF THE NEW VARIETY

Figure 1:
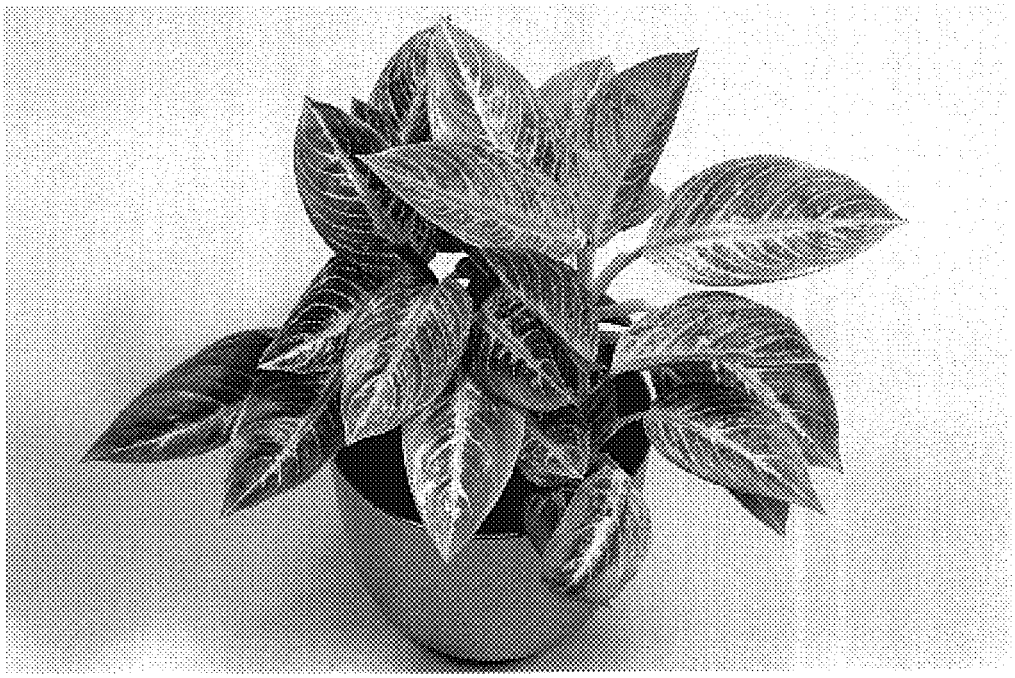
FIG. 1 shows the overall plant habit.
Figure 2:
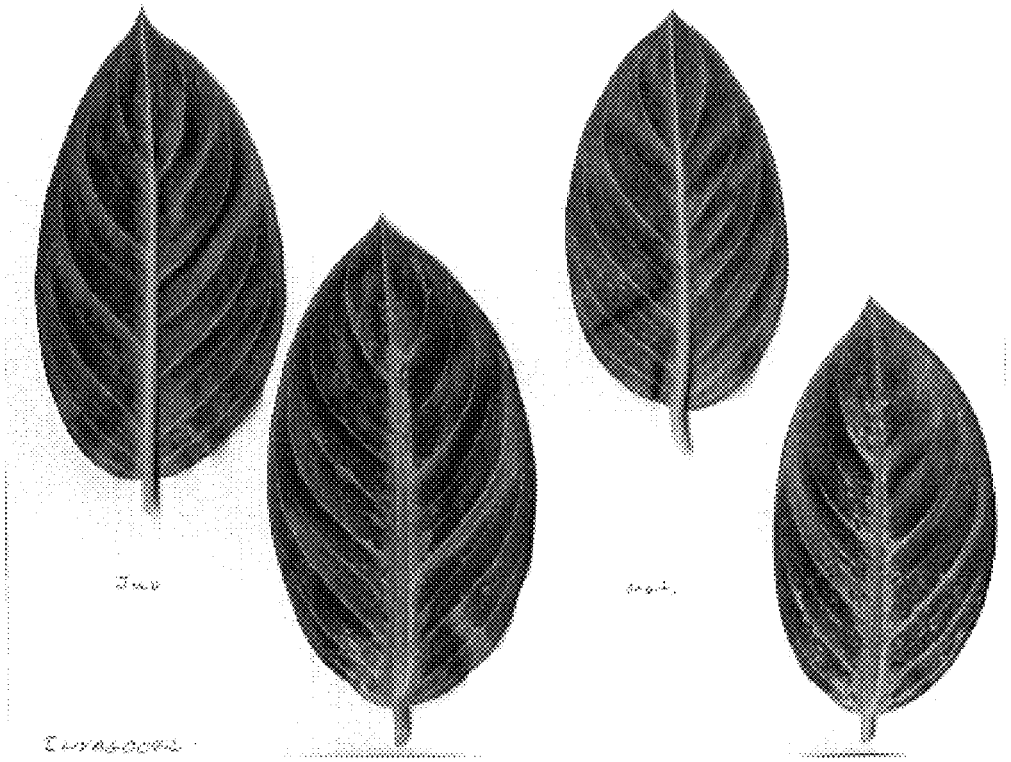
FIG. 2 (from left to right) shows the color of the lower surface of an immature leaf, the upper surface of an immature leaf, the lower surface of a mature leaf and the upper surface of a mature leaf.

The following detailed description sets forth the distinctive characteristics of 'TWYAG0042'. The data which define these characteristics were collected from asexual reproductions carried out in Apopka, Fla. The plant history was taken on 12 month-old plants started from a single four-leaf rooted cutting, still in a vegetative state and grown in Apopka, Fla. Rooted cuttings were planted in 15-cm pots and grown in a greenhouse in January 2007. The plants were pinched once. Color readings were taken under natural light. Color references are primarily to the R.H.S. Colour Chart of The Royal Horticultural Society of London (RHS) (2001).

DETAILED BOTANICAL DESCRIPTION

Classification:
*Family.*—Araceae.
*Botanical.*—*Aglaonema* hybrid.
*Common.*—Chinese Evergreen.
*Cultivar name.*—'TWYAG0042'.

Growth:
*Form.*—Upright and wider than tall; new leaves are held upright and mature leaves are held outward.

*Growth and branching habit.*—Leafy and compact; upright, branched and small in stature.

*Height* (*from soil to top of leaf plane*).—25 cm to 33 cm.

*Diameter* (*area of spread, as measured from leaf tip to leaf tip across the canopy*).—38 cm to 44 cm.

*Growth rate.*—Typical of commercial *Aglaonema* varieties.

*Vigor.*—Plants produce axillary branches and numerous leaves.

*Time to produce a finished flowering plant.*—About 12 months starting from a single 4-leaf rooted cutting with the plants pinched once in 15 cm pots.

*Root description.*—Abundant, fleshy and white with finer lateral branches.

*Number of divisions or clumps per year.*—About five 4-leaf cuttings per year.

*Durability of foliage to stresses.*—Foliage holds up well against damage from shipping and handling; plants are durable and have excellent indoor keeping quality.

*High temperature tolerance.*—About 104° F. For several hours without damage.

*Low temperature tolerance.*—About 55° F. for several hours without damage.

Stems:

*Number of branches per plant.*—About 17.

*Type of branching.*—Basal.

*Length* (*from soil line to junction of the newest two leaves*).—9 cm.

*Diameter* (*measured from the midpoint*).—1.0 cm.

Internode length.—0.8 cm to 1.6 cm.

*Color.*—Immature: RHS 145D. Mature: RHS 155D. Oldest stems: RHS 155D.

*Shape and appearances.*—Columnar, cylindrical and upright.

*Aspect.*—Vertical and upright.

*Strength.*—Sturdy and somewhat flexible.

*Axillary buds.*—Shape: Elliptic, flat to convex. Length: 0.58 cm. Width: 0.3 cm. Color: RHS 155C tinged with RHS 146C proximally.

Leaves:

*Arrangement.*—Alternate and simple; the leaves are arranged in a spiral along the stem; the leaf blade folds upward somewhat along the midrib.

*Quantity of leaves per stem.*—8.

*Immature leaf* (*newly expanded leaf*).—Color: Upper surface: Base color is between RHS 147A and RHS 146A; the leaf blade is marked, especially proximally, with small RHS 145C to RHS 145D coalescing spots and blotches; areas adjacent to the primary veins are often variably marked with RHS 145C to RHS 145D and occasionally tinged with RHS 55C; areas adjacent to the midrib are marked with RHS 145C and between RHS 145D and RHS 150D and often variably tinged with RHS 55C. Lower surface: Base color is between RHS 147A and N RHS189A and has an overall cast of RHS 181C; the upper surface patterns and markings are visible through to the lower surface of the leaf; the leaf blade is marked with small coalescing RHS 181C spots; the areas adjacent to the midrib are RHS 181C.

*Mature leaf.*—Color: Upper surface: Base color is RHS 147A; the leaf blade is marked, especially proximally, with small coalescing spots and blotches between RHS 145D and RHS 150D; the areas adjacent to the primary veins are often marked with RHS 145D and occasionally tinged with RHS 55C; the areas adjacent to the midrib are marked with RHS 150D and often variably tinged with RHS 55C. Lower surface: Base color is RHS 147A and has an overall cast of RHS 181D; the upper surface patterns and markings are visible through to the lower surface of the leaf; the leaf blade is marked with small coalescing RHS 181D spots; areas adjacent to the midrib are RHS 181D to RHS 49B.

*Length.*—12.0 cm to 14.0 cm.

*Width.*—Flattened: 5.5 cm to 7.4 cm. Not flattened: 5.4 cm to 6.8 cm.

*Shape.*—Elliptic to ovate.

*Apex.*—Acuminate to cuspidate.

*Base.*—Obtuse.

*Margin.*—Smooth, entire and mostly flat with some broad undulations.

*Texture.*—Upper surface: Smooth; new leaves are shiny while mature leaves are slightly glossy to dull; Lower Surface: Smooth and glossy to dull, the leaf blade is convex between the main veins resulting in a textured appearance.

*Pubescence.*—Absent.

*Venation pattern.*—Pinnate and radiating outward from the midrib in a herringbone arrangement.

*Venation color.*—Immature leaf (newly expanded leaf): Upper surface: Primary veins: RHS 145C to RHS 145D and occasionally tinged with RHS 55C. Midrib: RHS 55B to RHS 55C. Lower surface: Primary veins: RHS 181C to RHS 181D and tinged with RHS 49B. Midrib: RHS 49B to RHS 49C. Mature leaf: Upper surface: Primary veins: Between RHS 145D and RHS 150D occasionally tinged with RHS 55C. Midrib: RHS 55A to RHS 55B. Lower surface: Primary veins: RHS 49B to RHS 49C. Midrib: RHS 49C to RHS 49D.

Petioles:

*Aspect.*—Vertical and upright when newly expanded and becoming curved outward to about 45 degrees with maturity.

*Length.*—8.5 cm.

*Width* (*not flattened*).—1.0 cm.

*Diameter.*—Distal: 0.38 cm. Proximal (petiole and petiole sheath clasp the stem proximally): Flattened: 2.0 cm. Not flattened: 0.70 cm.

*Color.*—Distal (between the top of the wing and the base of the leaf): RHS 56A to RHS 56B. Proximal: RHS155D and tinged with RHS 56B. Areas adjacent to the stem: RHS 155D.

Wing:

*Length.*—6.8 cm.

*Diameter.*—Mid-point: 0.7 cm. Base: 1.0 cm. Depth: 0.5 cm.

*Color.*—Inside: RHS 155D. Outside: RHS 155D and tinged with RHS 56D. Area adjacent to the stem: RHS 155D.

Cataphylls:

*Length.*—5.0 cm.

*Width.*—1.0 cm.

*Shape.*—Lanceolate, one or two-keeled and translucent.

*Texture.*—Inner surface is smooth and shiny while outer surface is glossy.

*Apex.*—Cuspidate.

*Base.*—Clasps the peduncle or stem. Inner and outer surfaces: Translucent;

*Color.*—RHS N155B overall and tinged with RHS 49B toward the apex.

Inflorescence: None observed.

Reproductive organs: None observed.

Fruit and seed set: None observed.

Disease and insect resistance: Typical of *Aglaonema* species; no particular susceptibility or resistance to pests or diseases noted.

COMPARISON WITH KNOWN VARIETIES

'TWYAG042' differs from the commercial variety 'TWYAG0003' (U.S. Plant Pat. No. 17,673) in that 'TWYAG0042' is narrower (38 cm to 44 cm vs 55 cm) and has smaller leaves than 'TWYAG0003'. In addition, 'TWYAG0042' has fewer spots on its leaves and its leaf midribs are a different shade of pink (RHS 55A to RHS 55B) than the leaf midribs of 'TWYAG0003' (RHS 54D).

I claim:

1. A new and distinct cultivar of *Aglaonema* plant as shown and described herein.

* * * * *